(12) United States Patent
Cox

(10) Patent No.: US 6,862,301 B2
(45) Date of Patent: Mar. 1, 2005

(54) TUNABLE LASER ASSEMBLY

(75) Inventor: James Allen Cox, New Brighton, MN (US)

(73) Assignee: Finisar Corporation, Sunnyvale, CA (US)

( * ) Notice: Subject to any disclaimer, the term of this patent is extended or adjusted under 35 U.S.C. 154(b) by 112 days.

(21) Appl. No.: 10/037,010

(22) Filed: Dec. 31, 2001

(65) Prior Publication Data

US 2003/0123495 A1 Jul. 3, 2003

(51) Int. Cl.[7] .................................................. H01S 3/10
(52) U.S. Cl. ....................................................... 372/20
(58) Field of Search .............................. 372/20–21, 92, 372/53

(56) References Cited

U.S. PATENT DOCUMENTS

| | | | |
|---|---|---|---|
| 3,774,121 A | * 11/1973 | Ashkin et al. ................. 372/53 |
| 4,577,321 A | 3/1986 | Carney et al. |
| 4,637,122 A | 1/1987 | Carney et al. |
| 4,695,790 A | 9/1987 | Mathis |
| 4,696,012 A | * 9/1987 | Harshaw ....................... 372/99 |
| 5,091,933 A | 2/1992 | Katz |
| 5,216,680 A | * 6/1993 | Magnusson et al. .......... 372/20 |
| 5,392,308 A | * 2/1995 | Welch et al. .................. 372/92 |
| 5,598,300 A | 1/1997 | Magnusson et al. |
| 6,055,262 A | 4/2000 | Cox et al. |
| 6,067,391 A | 5/2000 | Land |
| 6,091,504 A | 7/2000 | Walker et al. |
| 6,154,480 A | * 11/2000 | Magnusson et al. .......... 372/96 |
| 6,192,064 B1 | * 2/2001 | Algots et al. ................. 372/99 |
| 6,274,879 B1 | 8/2001 | Best-Timmann ............ 250/573 |
| 6,324,193 B1 | * 11/2001 | Bourzeix et al. ............. 372/20 |
| 6,459,709 B1 | * 10/2002 | Lo et al. ........................ 372/20 |
| 6,567,435 B1 | * 5/2003 | Scott et al. ............. 372/29.021 |
| 2001/0019563 A1 | * 9/2001 | Hatori ........................... 372/21 |
| 2001/0036206 A1 | * 11/2001 | Jerman et al ................. 372/20 |
| 2002/0024979 A1 | * 2/2002 | Vilhelmsson et al. ......... 372/20 |

FOREIGN PATENT DOCUMENTS

| | | | |
|---|---|---|---|
| EP | 1139523 A2 | 10/2001 | ............. H01S/5/14 |
| JP | 56126994 | 10/1981 | ............. H01S/3/10 |

OTHER PUBLICATIONS

Fehér, M. et al., "Optoacoustic Trace–Gas Monitoring with Near–Infrared Diode Lasers", *Applied Optics*, vol. 33, No. 9, pp. 1655–1658 (Mar. 20, 1994).

Shine, B. et al., "Diode Lasers Sing Spectroscopy's Tune", *Photonics Spectra*, pp. 138–142 (Mar. 1997).

Sneider, J. et al., "Photoacoustic Gas Detection Based on External Cavity Diode Laser Light Sources", *Optical Engineering*, vol. 36, No. 2, pp. 482–486 (Feb. 1997).

(List continued on next page.)

Primary Examiner—Don Wong
Assistant Examiner—Hung T Vy
(74) Attorney, Agent, or Firm—Workman Nydegger

(57) ABSTRACT

A tunable laser assembly, including a laser, a mirror, and a grating, wherein said grating is pivotably mounted between said laser and said mirror, wherein movement of said grating relative to said laser varies the wavelength of the energy emitted from the laser. A tunable laser assembly, including a laser comprising an emission surface, a top portion and a bottom portion, the cavity top portion being transparent to energy emitted from the laser, a detector positioned in the cavity, and a grating, pivotably mounted adjacent the laser, the grating cooperatively transmitting energy emitted from the laser to the detector, wherein changing the angle of the grating changes the wavelength of the energy incident upon the detector.

17 Claims, 11 Drawing Sheets

OTHER PUBLICATIONS

Sugihwo, F. et al., "Low Threshold Continuously Tunable Vertical–Cavity Surface–Emitting Lasers with 19.1 nm Wavelength Range", *Appl. Phys. Lett.*, vol. 70, No. 5, pp. 547–549 (Feb. 3, 1997).

Wang, S. et al. ,"Theory and Applications of Guided–Mode Resonance Filters", *Applied Optics*, vol. 32, No. 14, pp. 2606–2613 (May 10, 1993).

Wang, S. et al., "Multilayer Waveguide–Grating Filters", *Applied Optics*, vol. 34, No. 14, pp. 2414–2420 (May 10, 1995).

Heim, P.J.S. et al., "Single–angled–facet laser diode for widely tunable external cavity semiconductor lasers with high spectral purity," Electronics Letters, IEE Stevenage, GB, vol. 33, No. 16, Jul. 31, 1997, pp. 1387–1389.

Magnusson, R., et al., "New principle for optical filters," Applied Physics Letters, American Institute of Physics, New York, U.S. vol. 61, No. 9, Aug. 31, 1992, pp. 1022–1024.

Kazharsky, Oleg, et al., "Broad Continuous Frequency Tuning of a Diode Laser with an External Cavity," Optics Communications, North–Holland Publishing Co., Amsterdam, NL, vol. 137, No. 1–3, Apr. 15, 1997, pp. 77–82.

* cited by examiner

TUNABLE LASER ASSEMBLY

FIELD OF THE INVENTION

The invention relates generally to semiconductor lasers and assemblies using the same. More specifically, the invention relates to tunable laser assemblies that can be used in a number of applications, including for example, detector applications; such as the qualitative and quantitative determination of fluids such as liquid and gaseous compounds in an ambient sample, and in optical communications applications.

BACKGROUND OF THE INVENTION

Tunable light sources have multiple and varied uses. Two particularly important applications for their use are chemical detection and optical communications applications.

The practical applications of chemical analysis now reach from the exotic environments of deep-sea exploration and outer space to the more mundane aspects of everyday life such as detecting emissions from a household gas furnace.

The Chemical and Biological Defense Information Analysis Center (CBIAC) has specifically identified forty-seven critical compounds and has begun the process of identifying various detection means, databases, and threshold limit values. The forty-seven compounds are grouped into eight categories: nerve agents, blood agents, toxins, blister agents, choking agents, incapacitating agents, riot control agents, and other. Of these, the first three are particularly important because of lethality at very low concentrations, and typically a variety of detection and discrimination means are required to cover all of the compounds.

Examples identified by CBIAC are shown below with threshold limit values (TLV). The required threshold values range over many orders of magnitude, but that the nerve agents, at the part per trillion (ppt) level, are by far the most stressing. It is estimated that approximately eighty percent of the compounds have TLVs greater than 1 part per billion (ppb).

Threshold Limit Values (TLVs) of Most-Lethal Compounds

| Compound [CAS Registry No.] | Agent Type | TLV |
| --- | --- | --- |
| Arsine [7784-42-1] | Blood | 50 ppb |
| Cyanogen Chloride [506-77-4] | Blood | 300 ppb |
| Hydrogen Cyanide [74-90-8] | Blood | 4700 ppb |
| Chloropicrin (PS) [76-06-2] | Choking | 100 ppb |
| Mustard (HD) [505-60-2] | Blister | 0.5 ppb |
| Methylphosphorothioate (VX) [50872-69-9] | Nerve | 0.8 ppt |
| IsopropylMethylPhosphonofluoridate (GB, sarin) [107-44-8] | Nerve | 16 ppt |
| Ethyl N,N-Dimethyl Phosphoramidocyanidate (GA) [77-81-6] | Nerve | 14 ppt |
| PinacolylMethylPhosphonofluoridate (GC) [96-64-0] | Nerve | 3 ppt |

Mass spectroscopy, gas chromatography, and nuclear magnetic resonance are popular techniques for these chemical agents because they provide both high sensitivity and excellent discrimination. However, good performance for all three techniques is achieved only in a laboratory environment using large instruments and controlled conditions, and, as such, these techniques do not readily scale to compact, low cost implementations with near-real-time response.

Two valuable chemical phenomena often relied on in the detection of a chemical species in any environment include optical transmission and absorbance. Transmission and absorbance share a common functionality with the direction of an energy source of known quantity into a gaseous or liquid sample. The energy passed through the sample is then measured to determine the change in energy given a relative transmission reading or absorbance depending on the analytical method used.

Infrared spectroscopy has also received considerable attention as a detection means for these compounds, but emphasis has been primarily in the fundamental absorption bands at longer wavelengths (>5 $\mu$m). However, a simple analysis, as well as a survey of absorption line strength databases, confirms that any compound containing hydrogen should have significant absorption line strengths in the 1–2 $\mu$m waveband. Furthermore, all but four of the critical compounds contain hydrogen (the exceptions are chlorine, cyanogen chloride, carbonyl chloride, and diphosgene), and thus the vast majority should have detectable signatures in the 1–2 $\mu$m waveband.

The wavelength of the laser emission is critical to the intended application. For example, in the detection of a given chemical analyte, it is well known that a discrete atom will absorb and/or transmit energy only when energy of the appropriate wavelength is directed at the analyte. The same is true of chemical compounds and mixtures of atoms and compounds. While the critical wavelength can often be represented as a range of limited size, there is most always an optimal discrete wavelength for a select analyte.

Given these realities, analysis of a sample drawn from an environment of complex origin can be a more sophisticated task than qualitatively determining the presence of a single analyte. However, one of the benefits of laser technology is that a discrete semiconductor laser can be tuned to traverse many wavelengths. The emission wavelength of a semiconductor laser can be varied through the use of magnetic fields or pressure as well as by changing the diode current or heat sink temperature. For example, Walker et al, U.S. Pat. No. 6,091,504 discloses a semiconductor laser made tunable by controllably varying the temperature of the laser. In turn, this causes the laser emissions to sweep through a range of wavelengths.

Tunable light sources are also of great significance to optical communications applications. In the "long-haul" telecommunications arena, the need to maximize the data carrying capacity means the need to maximize the speed of each individual transceiver channel. This implies the need for single mode fiber based links and also explains the trend toward Dense Wavelength Division Multiplexing (DWDM), where many channels, closely spaced in wavelength, are combined onto a single fiber.

However, DWDM systems require frequency stabilization, either with wavelength lockers or TE cooler feedback to control wavelength by controlling temperature. Very long reach links rely upon lasers emitting a DC signal that is then modulated with an external electro-optic modulator to minimize chirp penalty. Chirp is the shift in wavelength that occurs as a laser transitions from the off to the on state due to heating and bandfilling. A second driver is the desire to transmit data over the longest possible distance without requiring regeneration of the signal, with its associated optical to electrical (O–E) and E to O conversion. This means that higher power lasers are generally preferable.

The same requirement, along with the development of dispersion shifted fiber, has resulted in the shift in preferred wavelength from 1310 nm to 1550 nm. Formerly, the minimum in dispersion as a function of wavelength was at 1310 nm, while the minimum in absorption loss was at 1550 nm. The development of the new fiber has shifted this minimum in dispersion closer to 1550 nm, making it the preferred solution for long distance transmission.

Local metro networks are another optical communications application that utilize tunable laser sources. A metro network is a conglomeration of various services, such as voice/telephone, internet, corporate/campus computer networks, parts of cell phone and cable TV delivery, etc., provided in a metropolitan-size geographical region (typically 10 to 80 kilometers). Although operated by various institutions/companies, it is possible that transmission of these services share common installations. Presently many of these services are delivered by electrical cables and in part by fibers with a single carrier wavelength. However, the demand for bandwidth is growing rapidly.

Many of the service providers are turning to technologies that will provide maximum bandwidth such as high-speed transmission (10 Gbit/s, 40 Gbit/s) and wavelength multiplexing. The same considerations exist as above, but cost becomes a greater consideration. The components are still driven towards 1550 nm, moderate optical output power, and the use of wavelength division multiplexing ("WDM").

WDM is a means to increase the data rate (bandwidth) in a single fiber transmission line by transmitting several channels simultaneously in the same fiber, but the channels are transmitted on slightly separated wavelengths (each channel has its own uniquely assigned wavelength). For this, a separate laser source is generally needed for each wavelength (channel), and the wavelength must be tightly controlled to be constant over temperature variations.

One method of generating well defined levels of energy is through the use of lasers. Lasers, and semiconductor lasers in particular, are capable of emitting energy having wavelengths of great regularity. Semiconductor lasers are distinguished by quantum transitions that are associated with the band properties of the materials used to fabricate the laser device. These lasers are also known to be of small size having an active region that is very narrow. Further semiconductor lasers are distinguished by very short photon lifetimes allowing for modulation at high frequencies.

The laser emission wavelength is highly dependent on the material used to fabricate the laser. Lasers are generally fabricated from material found in periods III–V of the periodic table formed into ternary and quaternary compounds. Emission wavelengths can range from ultraviolet through visible to near infrared and infrared. Around 1.3 $\mu$m to 1.55 $\mu$m wavelength the energy emitted in for example a fiber is characterized by low loss and low dispersion.

In the past, the tuning of semiconductor lasers has been accomplished through any number of mechanisms. One method for implementing tunable lasers is to provide an array of discrete lasers, each emitting a separate, fixed wavelength, the individual wavelengths being selectable through an x-y addressable switch. This approach is effective and can provide spectral power for the given wavelength. However, this type of laser array is not truly tunable and thus cannot provide the flexibility to discern a wide variety of chemicals or accurately determine the make up of a complex gaseous or liquid mixture.

A further method of fabricating a tunable laser, depicted in FIG. 1, is to use a microelectro-mechanical actuated top mirror to tune the resonant cavity of a vertical cavity surface emitting laser. This type of structure has been reported to around 20 nm of tunable range. However, the power emitted by the laser was also reported to only be in the range of a few milliwatts; that is, of limited power.

Even still with these developments, there is a need for a more compact device including a laser, which is spectrally tunable over a range of wavelengths and supported by the intrinsic waveband of the laser.

SUMMARY OF THE INVENTION

The following summary of the invention is provided to facilitate an understanding of some of the innovative features unique to the present invention, and is not intended to be a full description. A full appreciation of the various aspects of the invention can be gained by taking the entire specification, claims, drawings, and abstract as a whole.

In accordance with the invention, there is provided a tunable laser assembly, including: a laser, a mirror, and a grating, which is pivotably mounted between the laser and the mirror wherein movement of the grating relative to the laser varies the wavelength of the energy emitted from the laser. It will become apparent to those skilled in the art that the grating can be rigidly or semi-rigidly mounted in all embodiments described herein. The invention also includes a tunable laser assembly, which includes a tunable laser as described above, a sample volume, and a detector wherein movement of the grating varies the wavelength of the energy transmitted from the laser into the sample volume and directed onto the detector thereby producing a signal characteristic of the spectral absorption by a chemical in the sample volume.

Another aspect of the invention includes a tunable laser assembly for detection and discrimination of chemical fluids, that includes a vertical cavity surface emitting laser, a detector positioned beneath the laser, and a grating, wherein the grating cooperatively transmits energy emitted by the laser to the detector, and the grating is pivotably mounted adjacent to the laser. This aspect of the invention also includes a tunable laser assembly for detection of chemical fluids, that includes a laser having an emission surface, collimating optics positioned adjacent the laser emission surface, a cavity having a top portion and a bottom portion, wherein the cavity top portion is transparent to energy emitted from the laser, a detector positioned in the cavity, and a grating, which is pivotably mounted adjacent the cavity, wherein the grating cooperatively transmits energy emitted from the laser to the detector, and changing the angle of the grating changes the wavelength of the energy incident upon the detector. This aspect of the invention also includes a tunable laser assembly for detection of chemical fluids, including: a vertical cavity surface emitting laser having an emission surface, a cavity positioned adjacent the laser, wherein the cavity has a top portion and a bottom portion, the top portion being transparent to energy emitted by the laser, a detector positioned in s the cavity, a highly reflective mirror positioned adjacent the laser, and a grating pivotably mounted above the laser, wherein the grating cooperatively functions with the laser and the highly reflective mirror transmitting energy emitted from the laser to the detector, wherein changing the angle of the grating changes the wavelength of the energy incident upon the detector.

Another aspect of the invention includes a tunable laser assembly including: a laser, a highly reflective mirror, a waveguide or optical fiber, and a grating pivotably mounted between the laser and the highly reflective mirror, wherein the grating cooperatively functions with the laser and the highly reflective mirror to transmit energy emitted from the laser into the waveguide or optical fiber, wherein changing the angle of the grating changes the wavelength of the energy launched into the waveguide or optical fiber.

The invention provides a tunable laser device and methods of using the device, for example, as a means of detecting and identifying chemical compounds or for use in telecommunications applications. The invention integrates vertical cavity surface emitting laser (VCSEL) technology with microelectro-mechanical system (MEMS)-based actuators and sensors. The invention provides a laser-based sensor—a VCSEL—tunable with MEMS actuators in the appropriate spectral range, Si micromachined sensors, and in one embodiment, mesoscopic pumps for gas concentration—to detect and discriminate chemical compounds at the required threshold levels.

More specifically, the invention provides a device and technique for achieving continuous tunability in a semiconductor laser, operated in external cavity configuration, for the range of wavelengths lying within the gain envelope of the active material comprising the laser. Applicable semiconductor laser types include both vertical-cavity surface-emitting lasers VCSELs and in-plane edge-emitting lasers. The invention integrates semiconductor laser technology with MEMS-based actuators controlling guided-mode grating resonant filter technology. The invention is amenable to high-volume, low-cost production. The invention is not restricted to specific spectral bands of semiconductor lasers, such as 850 nm or 1550 nm.

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the scope of the invention will become apparent to those of skill in the art from the detailed description of the invention and claims that follow.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

It should be understood that the drawings are not necessarily to scale and that the embodiments are illustrated using graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PREFERRED EMBODIMENTS

In accordance with the invention, there is provided a tunable laser apparatus including a source of spectrally tunable laser energy, which is tunable over a range of wavelengths through the use of a guided mode grating resonant filter. The invention also comprises a vertical cavity surface emitting laser positioned adjacent a sample containment volume under which is positioned a detector of appropriate type and size.

Figure 2:
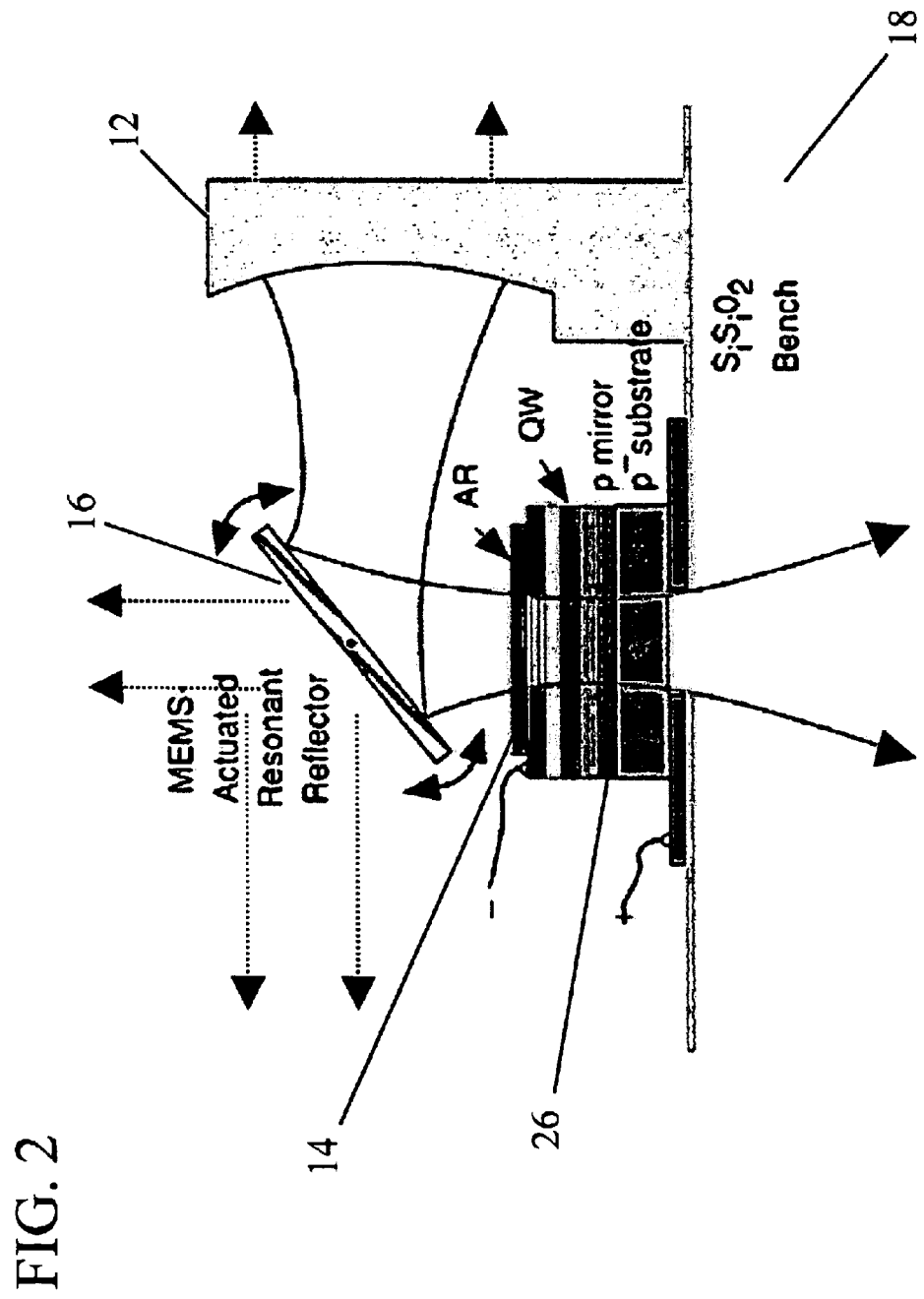
FIG. 2 is a cross sectional view of one embodiment of a tunable laser assembly in accordance with one aspect of the invention.

One preferred embodiment of the invention is shown in FIG. 2. A mirror 12 with a highly reflective coating is positioned adjacent a vertical cavity laser 14 having a highly reflective bottom mirror 26. The energy produced in the laser 14 may be directed out in one of four directions as depicted in FIG. 2 by the dashed lines. The direction of output is chosen by modifying the reflectivity of either mirror 12, 16, or 26 to make the reflectivity of the chosen direction slightly less than the others.

Positioned above the laser is a grating 16 which can be moved or pivoted about an axis, the axis running parallel to the top of the laser. Positioned beneath the laser is a supporting bench or substrate 18. Substrate 18 can be used to fix the assembly in place. For purposes of optical transmission, the substrate 18 can be fabricated from silicon or a silicon oxide. The ease and amenability of silicon and its oxides to physical and chemical fabrication processes also make it desirable for use in the invention.

In use, the invention can comprise any number of different types of lasers or laser arrays. The laser 14 is the active region of the assembly and functions to provide the source of energy, which is then tuned to the desired wavelength by the grating 16 or filter. The laser can be a vertical cavity laser such as a proton implanted (e.g., H+) confined or an oxide confined laser. Side emitting lasers can also be used in the assembly of the invention. Further, the energy emitted from the laser can vary across well known wavelengths, examples of which include 850 nm, 980 nm, 1.3 µm, and 1.55 µm, among others.

Figure 1:
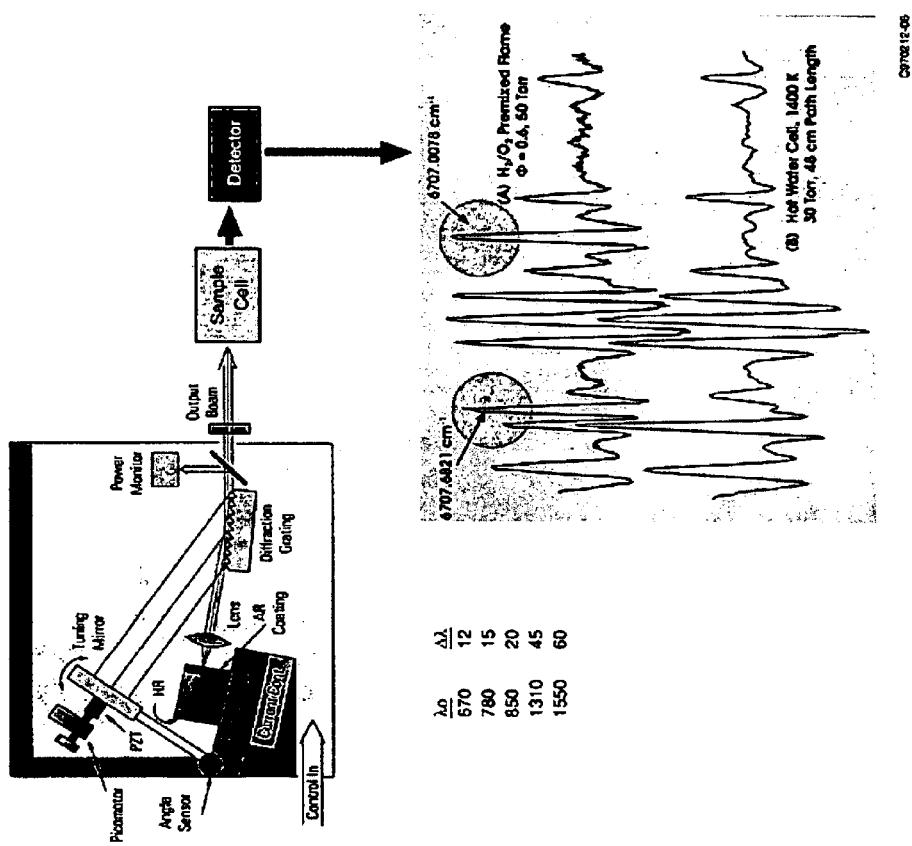
FIG. 1 is a cross-sectional view of a commercially available tunable laser representing the prior art, for use in the detection and distinction of chemical species.

The lasing action of the assembly occurs in the external cavity. The external cavity of the laser is the area of energy transmission between the Distributed Bragg Reflector 26 found in the stack of the vertical cavity laser and the concave mirror 12, FIG. 1. The wavelength of the laser generated energy that can be tuned ranges from about 0.4 to 5 µm while the relative wavelength can be tuned through about 50 nm.

Figure 3:
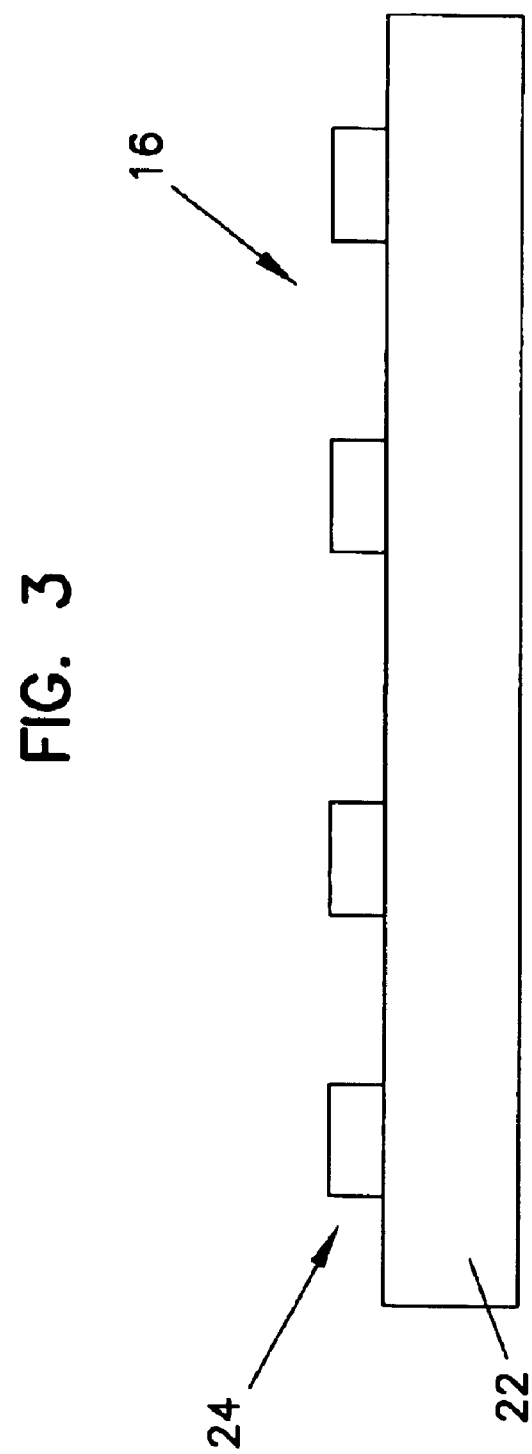
FIGS. 3 and 4 are cross-sectional views of a grating used in the invention, specifically a guided-mode grating resonant filter.

The grating or filter 16 can be used to vary the angle, wavelength, or polarization of the energy provided by the laser. As can be seen in FIG. 3, the grating 16, generally comprises substrate portion 22 and an active grating portion 24. The grating 16 is defined by several requirements. The grating 16 must comprise a planar wave guide; the refractive index of the grating core has to be greater than the other films in the substrate 22. The grating 16 also should be of zero order, which means that the period of the grating has to be less than the wavelength divided by the refractive index of the core.

Figure 4:
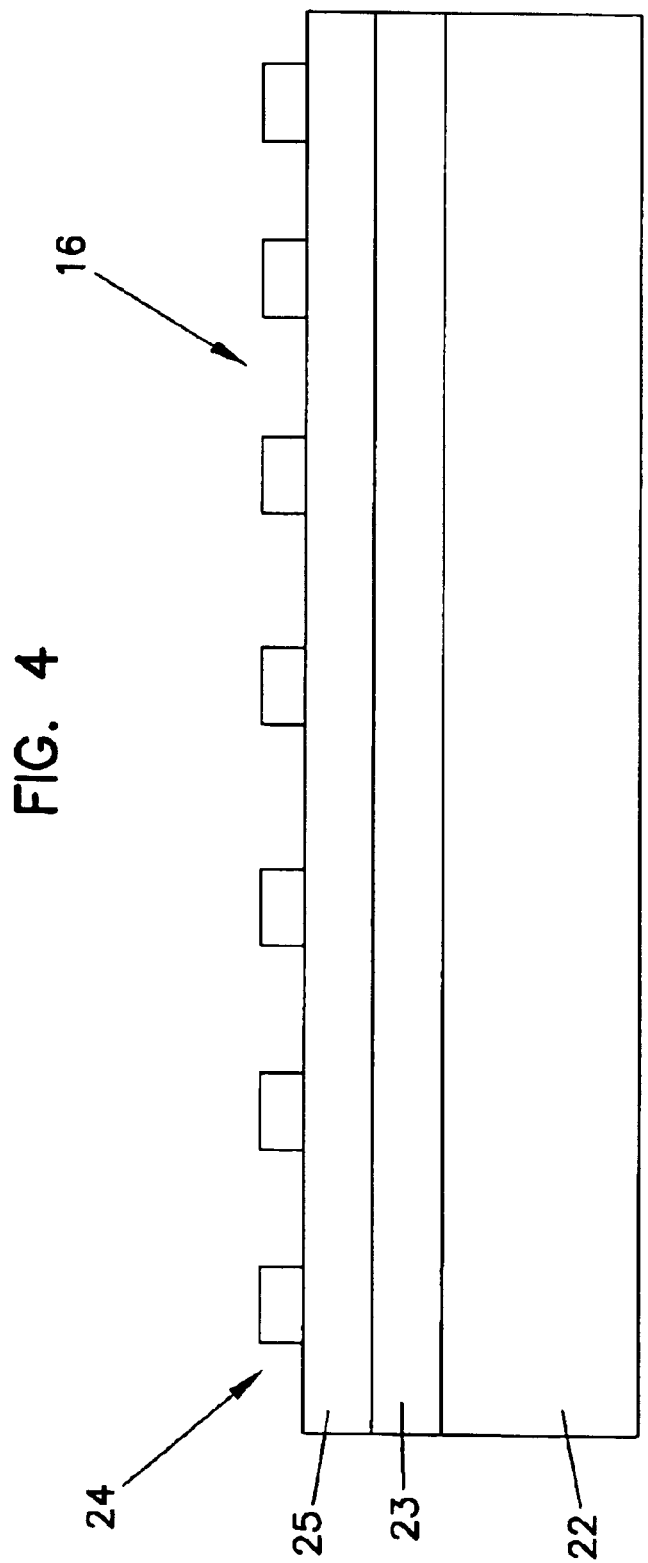

A further embodiment of a grating 16 in accordance with the invention can be seen in FIG. 4. This grating can be made using any dielectric or semiconducting materials. Generally the substrate 22 can be made of fused silica. Films 23 and 25 can be formed of oxides or oxide mixtures such as silicon oxides and titanium oxides. Either of films 23 or 25 can be formed into the grating core by adjusting the mix of oxides as the film is deposited. In one example, the substrate 22 had a refractive index of 1.453, with film 23 having a thickness of 0.106 μm and a refractive index of 2.016. In this particular example, film 25 was formed as the core of the grating with a thickness of 0.100 and a refractive index of 2.106.

The grating layer 24 can be formed of materials such as for example, silicon or silicon oxides which can then be patterned and etched. In the particular example, the grating layer 24 had a thickness of 0.168 μm and a refractive index 1.485 providing a period of 480 nm.

A grating 16 in accordance with one aspect of the invention is a guided-mode resonant reflective filter (GMGRF). A GMGRF has properties nearly ideal for precise tuning of laser diodes; that is very high (~100%) in-band reflectance, very large (~30 dB) out-of-band suppression, very narrow (~0.1 nm) bandwidth, high polarization selectivity, and high degree of tunability with incident angle (~10 nm/deg).

For a given incident plane wave of wavelength λ, angle, and polarization, a grating of period Λ can be found such that a first diffractive order of the grating couples to the guided mode of the wave guide. However, because the refractive index of the wave guide core is periodically modulated, any excited guided mode also undergoes diffraction, and by reciprocity, one possible diffracted order must lie along the vector of the incident wave. By arranging the grating to support only the zero propagating order, energy of the guided mode diffracted out of the core can only lie along the direction of the incident wave, and through this coupling a resonance is established which can lead in principle to 100 percent reflectance in a very narrow spectral bandwidth.

The resonant wavelength is determined primarily by the grating period and the bandwidth primarily by the modulation of refractive index in the grating. Furthermore, for wavelengths outside the resonance region, the structure appears "homogenized" in its dielectric properties, and thus it can be considered approximately as a simple thin film structure with reflectance properties described by well known thin film expressions. In particular, it is possible to achieve antireflection conditions in the thin film structure away from the resonant wavelength. This resonant reflective filter exhibits ~7 nm/deg shift in its resonant peak with incident angle, and thus relatively small rotations of the mirror give a significant tuning range.

Having read this specification, those of skill in the art will understand that processes readily known for semiconductor fabrication can be used in making the grating 16. Additionally, a grating 16 can be fabricated and used consistent with this invention such as those disclosed in U.S. Pat. No. 6,055,262 (Cox et al.), U.S. Pat. No. 5,598,300 (Magnusson et al.), and U.S. Pat. No. 5,216,680 (Magnusson et al.) all of which are incorporated herein by reference.

Figure 5:
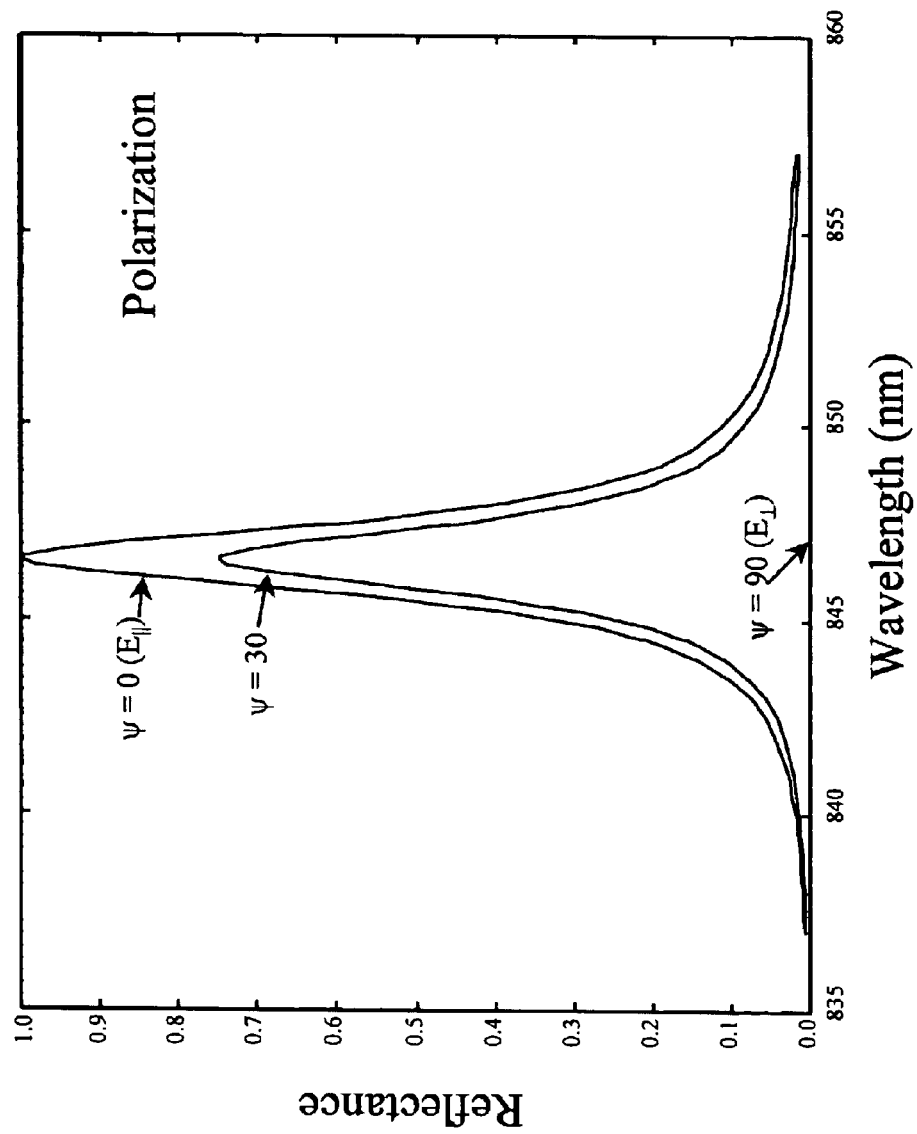
FIG. 5 depicts the polarization selectivity of a guided-mode grating resonant filter, with ψ being the angle between the grating lines and the electric field vector of the incident wave.
Figure 6:
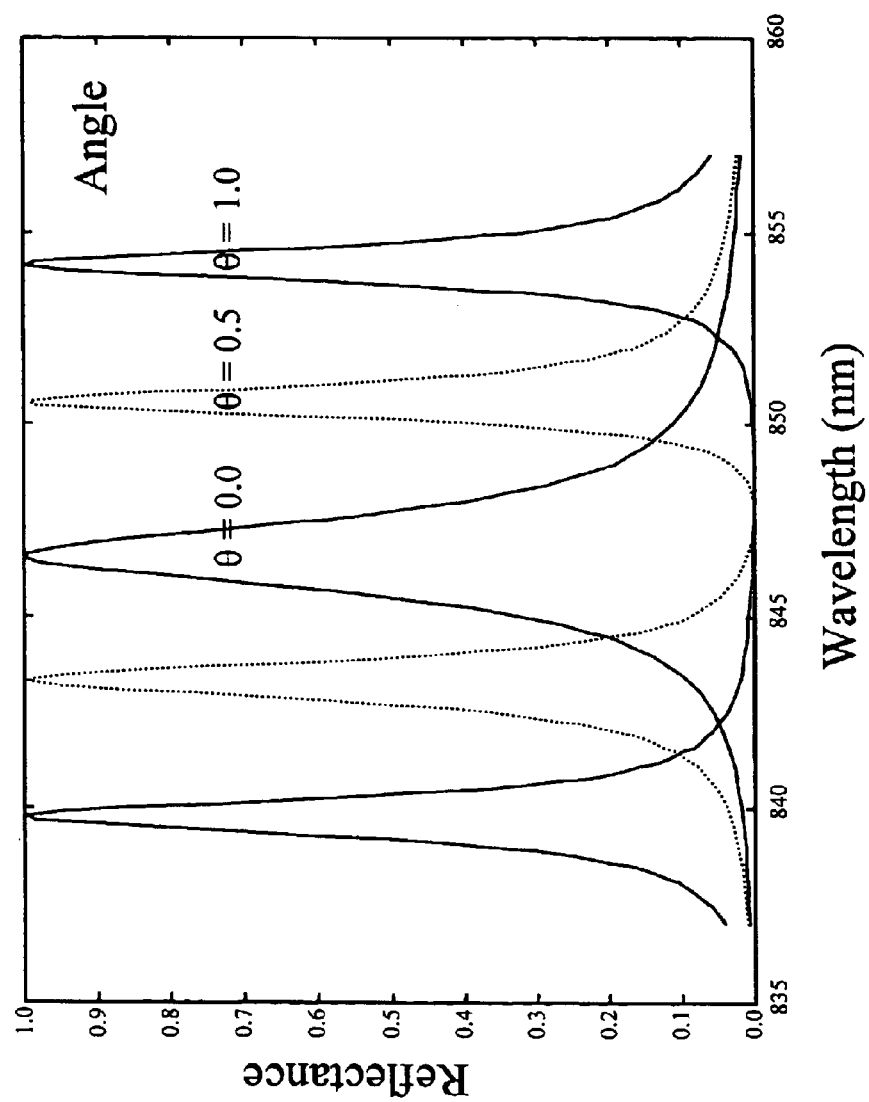
FIG. 6 depicts the variance of the filter reflectance with the incident angle of the incoming wave.
Figure 7:
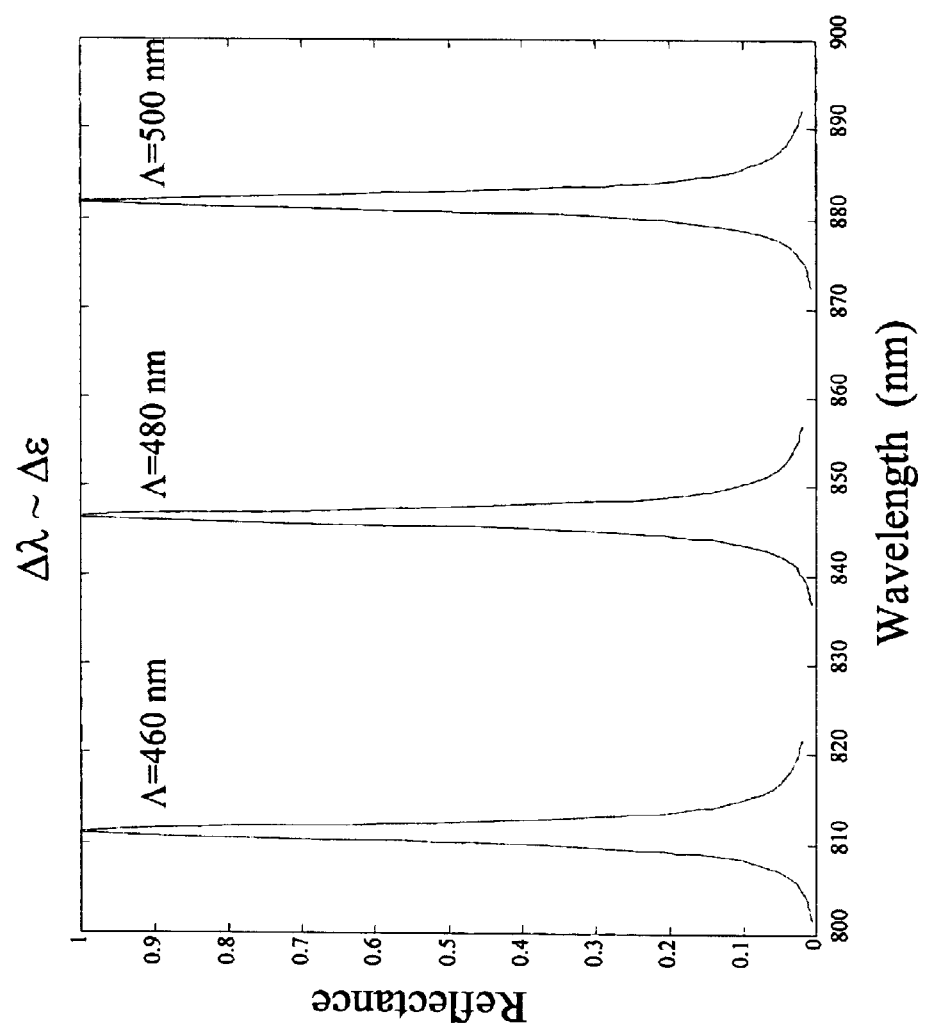
FIG. 7 depicts the selection of the wavelength of the peak reflectance by a guided-mode grating resonant filter.

In application, the grating 16 discussed above and disclosed in FIG. 4 can alter polarization, angle, and wavelength. FIG. 5 depicts the polarization selectivity of a grating 16. In that graph ψ is the angle between the grating lines and the electric field vector of the incident wave. Further, FIG. 6 shows how the filter reflectance varies with the incident angle of the incoming wave. This characteristic allows for the tuning of the laser wavelength. FIG. 7 depicts the selection of wavelength of peak reflectance by the period of grating 16. The assembly allows for wavelength control with reduced temperature sensitivity, polarization control, and transverse mode control.

The angular sensitivity of peak resonance must also be considered. An estimate of the peak shift with the change in grating angle can be calculated using the following equation: The mode matching condition is:

$$\beta = k\left(n_o \sin\theta_o \pm \left(\frac{\lambda}{v}\right)\right)$$

The wave guide observation is:

$$\beta \cong \frac{const}{\lambda}$$

Leading to an estimation of peak shift with a change in grating angle being determined by:

$$\frac{d\lambda_{res}}{d\theta_o} \cong \pm\left(\frac{\pi}{180}\right)^\wedge \cos\theta_o \, (nm/deg)$$

Figure 8:
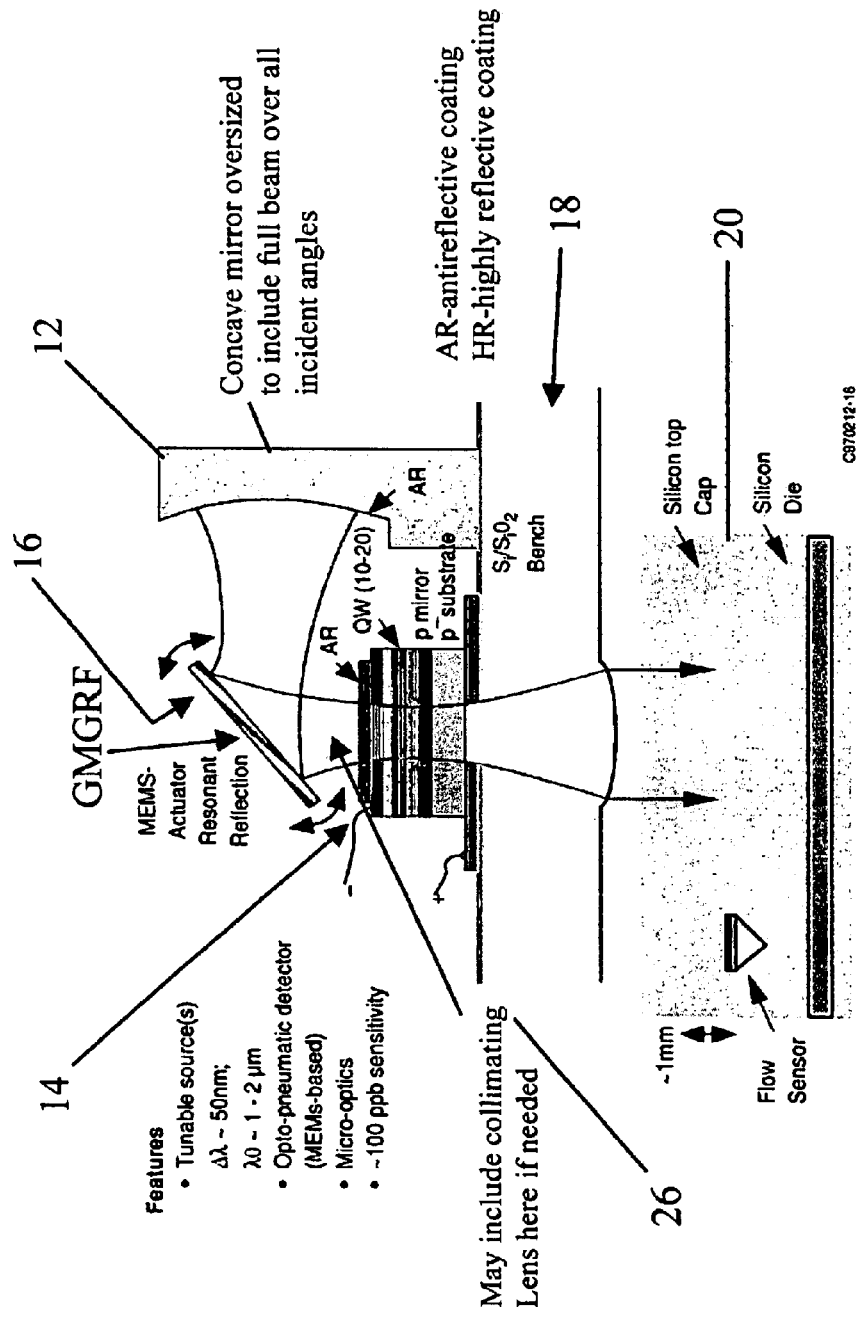
FIG. 8 is a cross-sectional view of one embodiment of the proposed tunable laser assembly integrated with a detection means.
Figure 9:
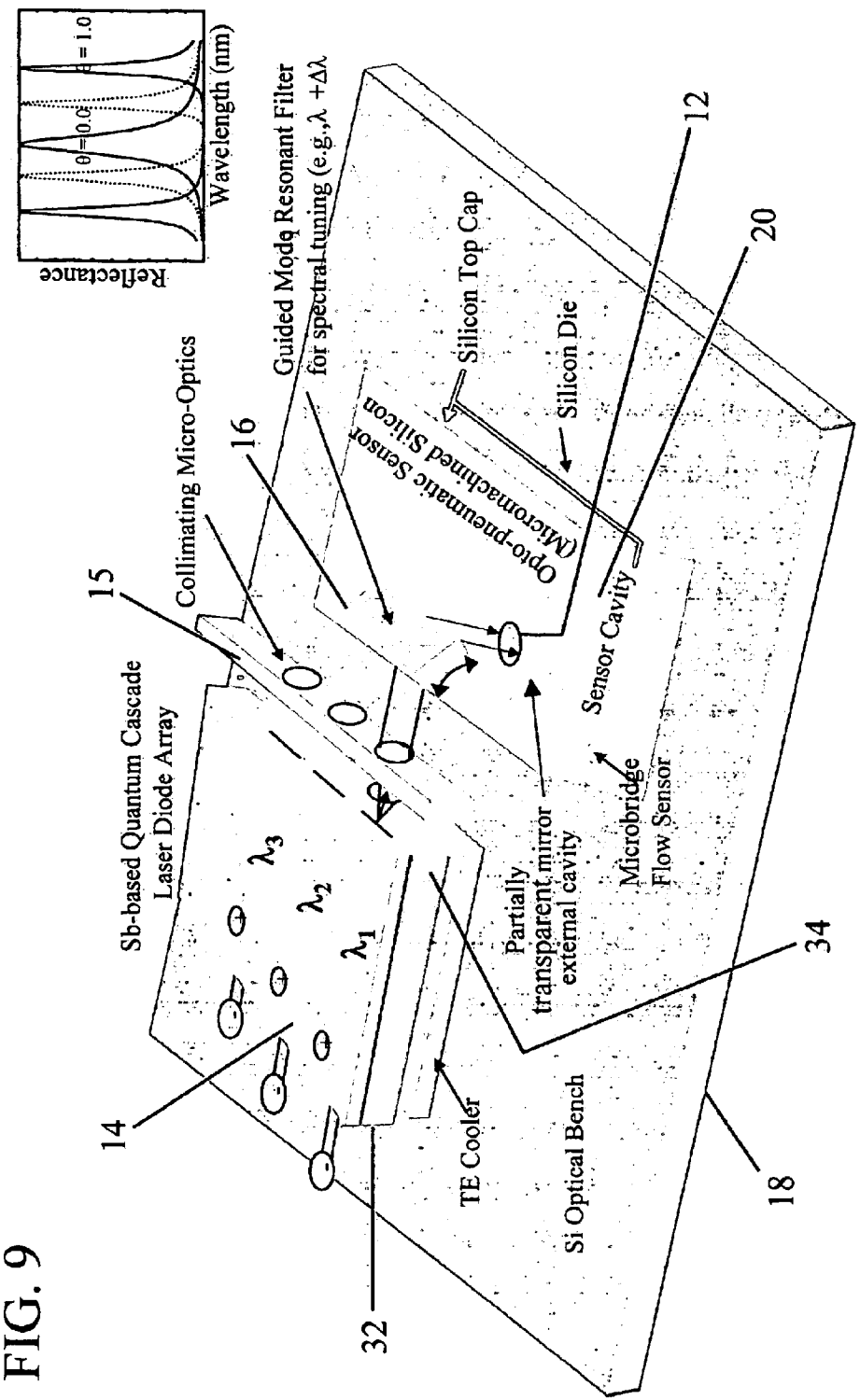
FIG. 9 is a perspective view of another embodiment of a tunable laser assembly in accordance with one aspect of the invention for use in the detection and distinction of chemical species.

Other elements of the invention include collimating optics, a sensor cavity, and a bench, support or substrate. Collimating optics 15, (FIG. 8), can be positioned between the laser and the grating in order to keep the laser energy from diverging during operation. A sensor cavity 20 can be seen in both FIGS. 8 and 9. The function of the sensor cavity is to contain fluid samples of gas or liquid. The upper portion of the sensor cavity 20 is transparent, preferably of silicon, thereby allowing the laser energy to reach the sample. Any number of mechanical, physical or chemical detectors can be used in accordance with the invention. For example, sensors or detectors relying on infrared, ultraviolet, mechanical, flow, or gravimetric principles are merely examples of sensors that can be used in accordance with the invention. As depicted in FIGS. 8 and 9 the sensor cavity is equipped with a flow sensor to gauge fluctuating in the flow of gas or liquid after contact with the laser energy.

Exemplary applications of a device in accordance with one aspect of the invention include detection of chemical components in fluids (gas or liquid) and optical communications.

Chemical Species Detection

FIG. 8 depicts a device of the invention for use in detection of chemical species. The device depicted in FIG. 8 has similar components as that discussed above in reference to FIG. 2, and are numbered similarly.

Adjacent the substrate 18 is a sample cavity 20 which can take any number of configurations. The substrate 18 is positioned immediately between laser 14 and the sensor cavity 20. Also present is a detector 21 in the cavity. The nature and type of sensor will vary depending on the chemical to be detected.

A further embodiment of the invention useful in chemical sensing can be seen in FIG. 9. In this embodiment, a side-emitting laser array 14 is provided. The side-emitting laser array 14 produces energy at a number of different wavelengths, $\lambda_1, \lambda_2 \ldots \lambda_n$. The individual lasers that make up side-emitting laser array 14 have an area comparable to the Distributed Bragg Reflector 26 present at back region 32 of side-emitting laser array 14. Energy is emitted from side-emitting laser array 14 at front surface 34.

This embodiment of the invention also has collimating optical fixture 15. Energy is emitted from front surface 34 of side-emitting laser array 14, goes through collimating optical fixture 15 and is directed toward guided-mode resonant filter 16. After interacting with guided-mode resonant filter 16, the energy is directed to mirror 12.

The mirror 12 is of a sufficient size and concavity that virtually all of the energy that leaves guided-mode resonant filter 16 is directed through mirror 12. Once the energy goes through mirror 12, it enters the sensor cavity 20. For ease of implementation the above components can be housed on an optical bench 18.

The external cavity in this embodiment of the invention is defined by the energy path as it goes from the back region 32 of side-emitting laser array 14 through side-emitting laser array 14, through front surface 34 of side-emitting laser array 14, through collimating optical fixture 15, through guided-mode resonant filter 16, then through mirror 12. The path from the back region 32 to mirror 12 defines the external cavity of this embodiment.

The side-emitting laser array comprises individual lasers. The wavelengths of these lasers are chosen based on the species to be detected. The difference in wavelength of these lasers is also chosen in part on the consideration of the width over which each individual laser can be tuned. For example, it would likely not be desirable to have two lasers with a difference in wavelengths of only 10 nm, because that difference could be obtained by tuning.

One advantage of embodiments like that depicted in FIGS. 8 and 9 is that the sensor system is that it can be packaged in a small volume suitable for deployment in any given application. The micromachined sensor can also be integrated with a mesoscopic pump to enhance the concentration of the sample in the sensor volume to attain the required sensitivity for the chemical agent of choice.

Figure 10:
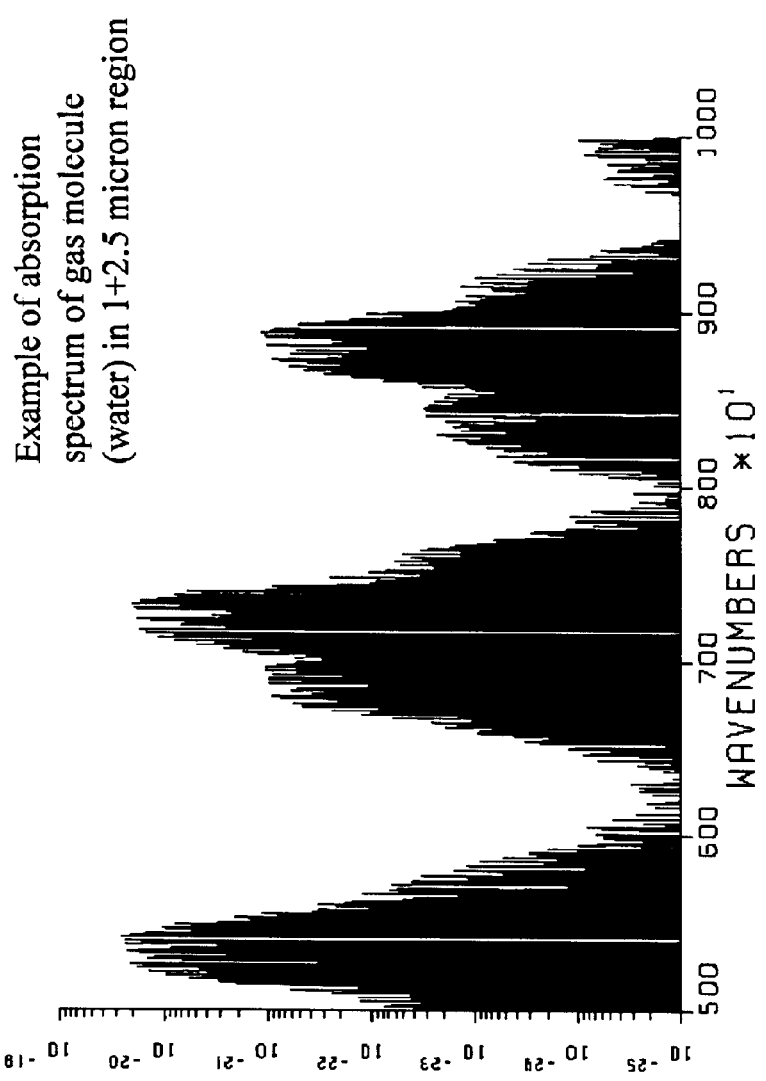
FIG. 10 is a graphical depiction of the absorption spectrum for water ($H_2O$).

Detection and discrimination of a great majority of the identified chemical compounds is based fundamentally on the observation that all compounds containing hydrogen exhibit significant absorption line strengths in the 1–2 $\mu$m waveband. Evidence of this is illustrated in the transmission spectra of water ($H_2O$), ammonia ($NH_3$), and benzene ($C_6H_6$). In each case there are at least two subwavebands with significant absorption: around 1400 nm and 1900 nm for both water and ammonia, and around 1200 nm and 1600 nm for benzene. All hydrogen-rich organic compounds that have been examined exhibit absorption peaks in the same subbands as benzene. A simple analysis based on typical covalent bond strengths and the atomic mass of hydrogen quickly shows the plausibility of absorption in this waveband of any hydrogen-bearing compound. Corroborating evidence is found in the line strengths of water tabulated in the HITRAN data base and plotted in FIG. 10. Here it can be seen that peak line strengths occur precisely at the transmission minima of water; furthermore, we see the magnitude of the line strengths approach $10^{-19}$ ($cm^2$/mol) $cm^{-1}$.

The detection of hydrogen-bearing compounds in the 1–2 $\mu$m waveband has been demonstrated with tunable laser diodes. In particular 8 ppb sensitivity in the detection of ammonia around 1600 nm (6528.773 $cm^{-1}$) using optoacoustic sensing with a 5 mW laser source, 3 second integration times, and wavelength modulation has also been demonstrated. The source wavelength was tuned, and modulated, by changing the temperature of the diode. Also measured was the line strength of this particular line and found it to be $\sim 2 \times 10^{-21}$ ($cm^2$/mol)$cm^{-1}$. By scaling this data, it was estimated that the same technique could yield ~100 ppt sensitivity for water around 1400 nm. This result thus shows significant potential for detecting chemical compounds with extraordinary sensitivity.

Further experiments using a tunable laser diode, FIG. 9, illustrate the ability to discriminate different compounds based on the detailed absorption spectra within the broad absorption subwavebands.

The technical results cited above demonstration the feasibility of detecting and discriminating hydrogen-bearing compounds using tunable laser sources in the 1–2 $\mu$m waveband with very high sensitivity. Our technical approach builds on these results by applying VCSEL technology to form the tunable sources and integrating them with MEMS actuators and micromachined Si opto-pneumatic sensors to achieve very compact sensors that can be produced in large volumes.

Optical Communications

Figure 11:
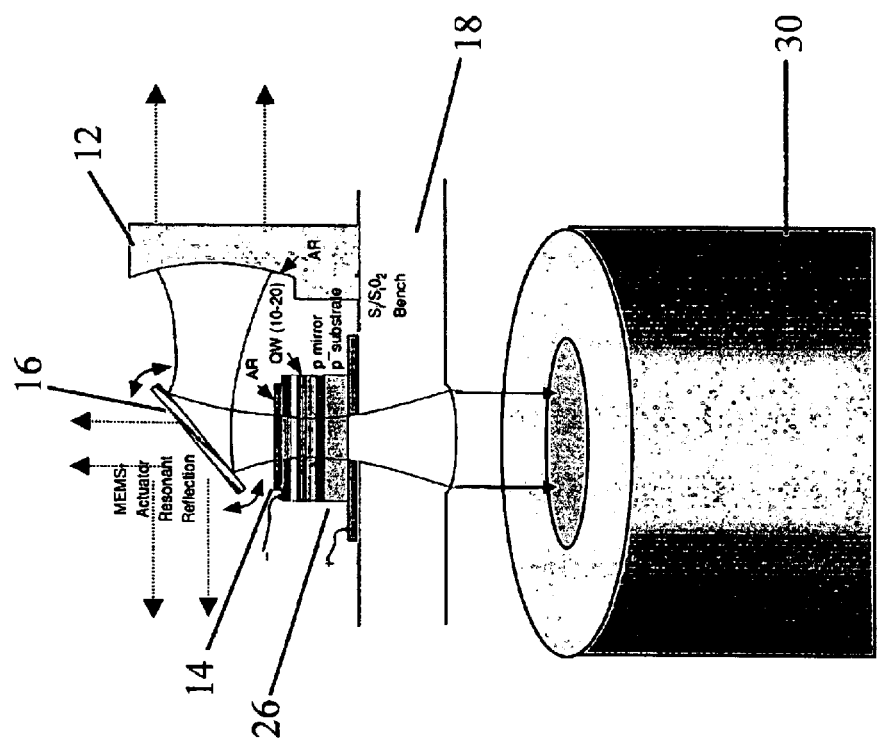
FIG. 11 is a cross-sectional view of a further embodiment of a tunable laser assembly in accordance with one aspect of the invention for use in optical communications.

A second exemplary application of a device of the invention is in optical communications, FIG. 11. The device depicted in FIG. 11 has similar components as that discussed above in reference to FIG. 2, and are similarly numbered.

Positioned adjacent substrate 18 is wave guide 30. Wave guide 30 can take any number of configurations, such as, optical fiber or a polymer-based wave guide. If wave guide 30 is an optical fiber, the device is easily amenable to use in optical communications.

A device configured in such a manner can provide multiple wavelengths of energy for direct coupling into an optical fiber. Tunable lasers in accordance with the invention, as exemplified above, can be utilized, without further modification, for this application. Tunable lasers of the invention could therefore easily take the place of standard non-tunable lasers that are commonly used in optical fiber communications applications.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The embodiments of an invention in which an exclusive property or right is claimed are defined as follows:

1. A tunable laser assembly, said assembly comprising:
   a laser that is a source of energy;
   a highly reflective bottom mirror;
   a convex mirror; and
   a guided-mode grating resonant filter, said guided-mode grating resonant filter pivotably mounted between said laser and said mirror, wherein at least some of said energy from said laser impinges upon said guided-mode grating resonant filter, which is configured to direct at least some of said energy upon said convex mirror, which is configured to direct at least some of said energy back to said guided-mode grating resonant filter, which is configured to direct at least some of said energy back to said laser, which is configured to direct at least some of said energy through said highly reflective bottom mirror, wherein movement of said guided-mode grating resonant filter relative to said laser varies the wavelength of energy emitted from the laser.

2. The assembly of claim 1, wherein said laser is a side emitting laser.

3. The assembly of claim 1, wherein said laser is a vertical cavity surface emitting laser.

4. The assembly of claim 1, wherein said convex mirror comprises a highly reflective coating.

5. A tunable laser assembly of claim 1, further comprising:
   a detector wherein said detector is positioned to receive energy from said laser.

6. The assembly of claim 5, wherein said laser is a side emitting laser.

7. The assembly of claim 5, wherein said laser is a vertical cavity surface emitting laser.

8. The assembly of claim 5, wherein said detector measures absorption of energy.

9. The assembly of claim 5, wherein said detector measures transmission of energy.

10. The assembly of claim 5, wherein said detector comprises a flow sensor.

11. The assembly of claim 5, wherein said guided-mode grating resonant filter is positioned above said laser and said assembly additionally comprises a cavity positioned beneath said laser, said detector being positioned within said cavity.

12. The assembly of claim 11, wherein said cavity is formed within a housing, said housing comprising a top portion and a bottom portion, said housing top portion being transparent to energy emitted by said laser.

13. The assembly of claim 5, additionally comprising collimating optics positioned between said laser and said guided-mode grating resonant filter.

14. A tunable laser assembly for detection of chemical fluids, said assembly comprising:
   a laser comprising an emission surface;
   a highly reflective bottom mirror;
   a cavity comprising a top portion and a bottom portion, said cavity top portion being transparent to energy emitted from said laser;
   a convex mirror
   a detector positioned in said cavity to receive energy from said laser; and
   a guided-mode grating resonant filter, pivotably mounted adjacent said laser, said guided-mode grating resonant filter cooperatively transmitting energy emitted from said laser to said detector, wherein changing the angle of said guided-mode grating resonant filter changes the wavelength of the energy incident upon the detector, and wherein at least some of said energy from said laser impinges upon said guided-mode grating resonant filter, which is configured to direct at least some of said energy upon said convex mirror, which is configured to direct at least some of said energy back to said guided-mode grating resonant filter, which is configured to direct at least some of said energy back to said laser, which is configured to direct at least some of said energy through said highly reflective bottom mirror.

15. The tunable laser assembly according to claim 14, wherein said laser is
   a vertical cavity surface emitting laser.

16. A tunable laser assembly according to claim 14, further comprising:
   a wave guide.

17. The assembly of claim 16, wherein said wave guide is an optical fiber.

* * * * *

UNITED STATES PATENT AND TRADEMARK OFFICE
CERTIFICATE OF CORRECTION

PATENT NO. : 6,862,301 B2
APPLICATION NO. : 10/037010
DATED : March 1, 2005
INVENTOR(S) : James Allen Cox It is certified that error appears in the above-identified patent and that said Letters Patent is hereby corrected as shown below:

Column 4
Line 51, before "the cavity" remove "s"

Column 8
Line 37, change "(FIG. 8)" to --(FIG. 9)--
Line 49, change "fluctuating" to --fluctuation--
Line 63, remove "21"

Column 10
Line 6, change "found it to be" to --it was found to be--

Column 11
Line 19, change "A" to --The--

Column 12
Line 34, change "A" to --The--

Signed and Sealed this

Third Day of April, 2007

JON W. DUDAS
*Director of the United States Patent and Trademark Office*